United States Patent [19]

Ding et al.

[11] Patent Number: 5,078,012

[45] Date of Patent: Jan. 7, 1992

[54] MOMENTUM METHOD FOR MEASURING UROFLOW PARAMETERS AND THE UROFLOW FLOWMETER

[75] Inventors: Tianhuai Ding; Zhengyi Zhang; Yuan Wei, all of Beijing, China

[73] Assignee: 501 Tsinghua University, Beijing, China

[21] Appl. No.: 521,825

[22] Filed: May 10, 1990

[30] Foreign Application Priority Data

May 15, 1989 [CN] China ................... 89102163

[51] Int. Cl.⁵ ............................................. G01F 1/28
[52] U.S. Cl. ............................. 73/861.74; 128/760
[58] Field of Search ........... 73/861.71, 861.74, 861.75; 128/760

[56] References Cited

U.S. PATENT DOCUMENTS

| | | | |
|---|---|---|---|
| 3,340,733 | 9/1967 | Lasher | 74/861.74 |
| 4,554,687 | 11/1985 | Carter et al. | 128/760 X |
| 4,732,160 | 3/1988 | Ask et al. | 128/760 |
| 4,841,782 | 6/1989 | Buchanan | 73/861.74 |

Primary Examiner—Herbert Goldstein
Attorney, Agent, or Firm—Rines and Rines

[57] ABSTRACT

A method and uroflowmeter apparatus for measuring uroflow parameters by flow impulse momentum, providing measurement and print out in real time of such parameters as the flow rate curve and of maximum flow rate, average flow rate, voided volume, voiding time, flow time, and time to maximum flow rate, necessary for medical diagnosis.

4 Claims, 3 Drawing Sheets

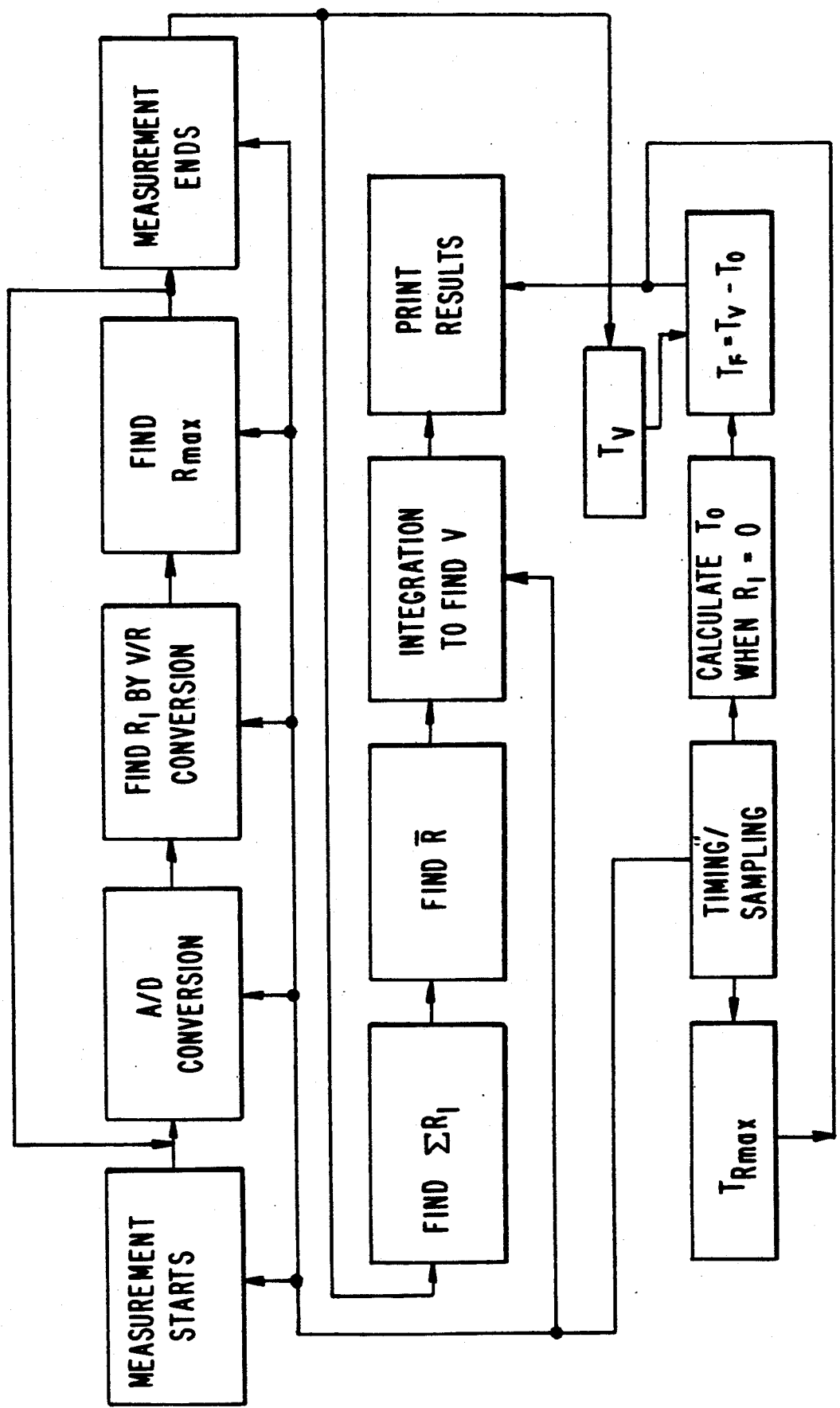

MOMENTUM METHOD FOR MEASURING UROFLOW PARAMETERS AND THE UROFLOW FLOWMETER

BACKGROUND OF INVENTION

This invention relates to instrument for human uroflowmetry. Uroflowmetry is an important part of urinary flow dynamics inspection, which requires measurement in real time of the flow rate, voiding time, voided volume and the flow rate as a function of time. These uroflowmetric results contribute not only to diagnosis of urinary obstruction, but also to objective evaluation of the effect of medical and surgical treatment and to the observation of the disease process.

There is no way except by means of accurate uroflowmeter measurements to obtain accurate and reliable uroflowmetric parameters. There are several manual or automatic uroflowmeters for medical use based on volume, gravity or dynamic balancing principles currently in use, but none of them provides satisfactory dynamic uroflowmetric results.

The principle of the URODYN 1000 automatic uroflowmeter made by Denmark DANTEC Electronics Ltd., for example, involves passing voided urinary flow is led onto a constant speed disk driven by a DC motor, with the electrical energy needed to keep the disk rotating at a constant speed being proportional to the flow rate. But the sensitivity of the flowmeter is not high, particularly at the starting or ending stages of voiding.

Object of Invention

The object of this invention, therefore, is to provide a novel uroflow measurement method and uroflowmeter with higher sensitivity, satisfactory to measure dynamic uroflowmetric parameters.

Summary of Invention

The purpose of this invention is to define the dynamic characteristics of urinary flow by impulse momentum. The principle is as follows. The urinary flow with certain speed impact on an elastic cantilever and produce a displacement of the cantilever. The displacement is proportional to the urinary flow impulse momentum. The displacement of the cantilever is detected by a displacement transducer (capacitive, inductive or eddy current type). The output electrical signal of the transducer, after conventional waveshaping, amplification, and A/D conversion, is fed to a microprocessor to be processed. A printer prints out the urinary flow curve.

DRAWINGS

The invention will now be described with reference to the accompanying drawings, FIG. 1 of which is a side elevation, partly sectionalized, of a preferred embodiment and mode of the uroflowmeter apparatus of the invention;

FIG. 6 is a schematic flow chart of the signal processing technique used with the system of FIG. 1.

DESCRIPTION OF PREFERRED EMBODIMENT

Figure 1:
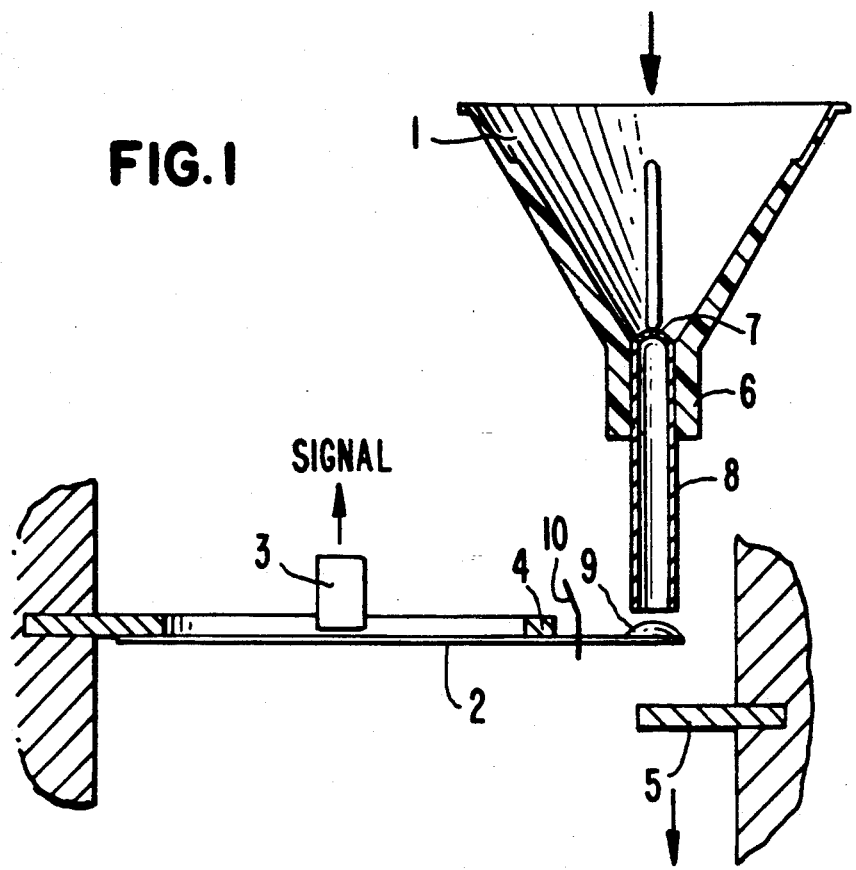
Figure 2A:
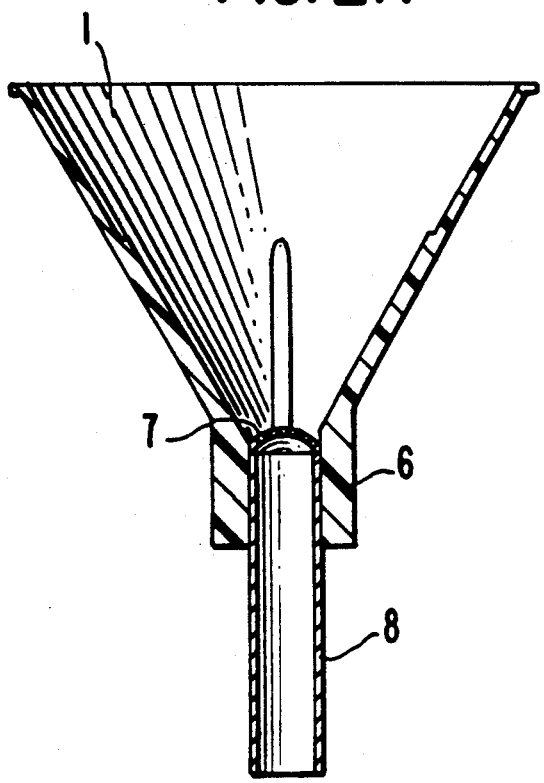
FIGS. 2A and 2B are respectively a transverse section and a top elevational view of the urinal portion of the apparatus of FIG. 1.
Figure 2B:
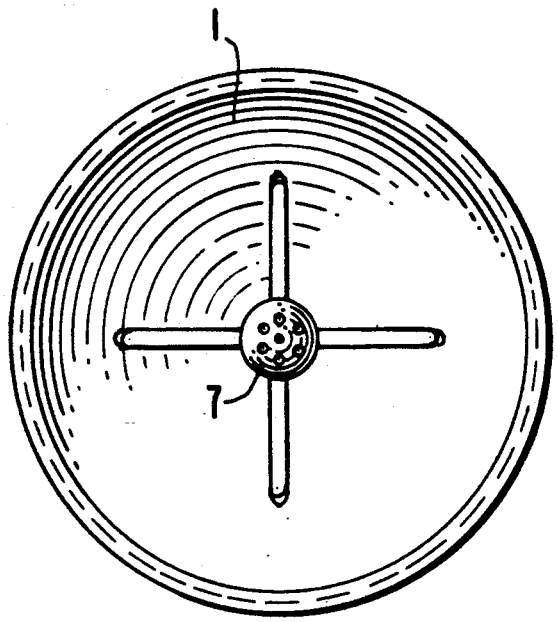

Referring to the drawings, FIG. 1 shows the overall construction of the uroflowmeter in preferred form with the abovementioned urinal illustrated at 1, the elastic cantilever at 2, a displacement measuring transducer at 3 for producing a signal corresponding to the cantilever displacement, and upper and lower displacement limiter stops for the cantilever 2 at 4 and 5, respectively. The body 6 of the urinal 1, FIGS. 1, 2A and 2B, is shown in conical form mounted upon a depending urinary flow tube 8, and with an upper apertured convex guiding surface 7.

Figure 3A:
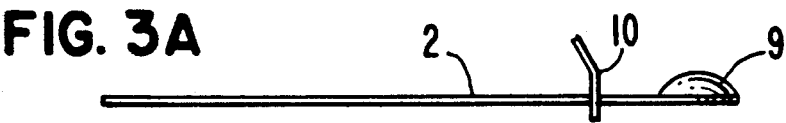
FIGS. 3A and 3B are respectively side and top views of the elastic cantilever of the apparatus.
Figure 3B:
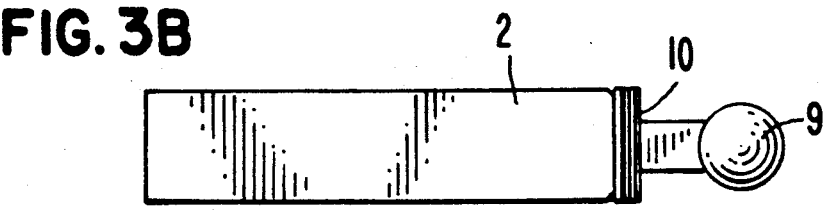
Figure 4A:
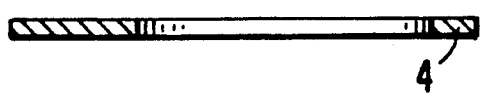
FIGS. 4A and 4B are respectively a transverse section and top view and FIGS. 5A and 5B, side and top views of displacement limiter stops for the cantilever.
Figure 4B:
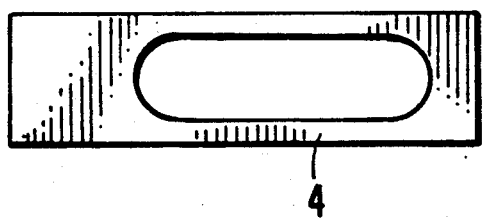
Figure 5A:
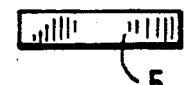
Figure 5B:
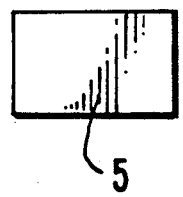

As more particularly shown in FIGS. 3A and 3B, the elastic cantilever 2 mounted below the slotted upper stop strip 4, FIGS. 4A and 4B, and extending therebeyond (to the right in FIG. 1), is provided with an upwardly extending splash deflector sheet 10 and a terminal extension comprising a convex urine flow impact surface 9. The lower cantilever beam displacement stop or limiter sheet is shown at 5, FIGS. 1, 5A and 5B.

The uroflowmeter transducer system and appropriate signal processing procedure of the invention will now be described.

After flowing into the urinal 1 the urine comes into contact with the apertured convex guiding surface 7 and flows through the apertures therein into and along the tube 8, impacting upon the terminal convex surface 9 and deflecting the elastic cantilever 2. The displacement of the cantilever is sensed by the transducer 3 and converted into an electrical signal which is sent to the signal processing system, FIG. 6. The limiter strips 4 and 5 protect the elastic cantilever from excessive displacement due to excessive flow and self-excited oscillation. The urinal and the limiters 4 and 5 may be made of hard plastic material and the elastic cantilever 2 of beryllium bronze. The sheet 10 may be made of corrosion resistant metals, such as stainless steel etc.

The working procedure or flow of the signal processing system, shown in FIG. 6, is as follows, with the uroflowmeter providing up to seven data outputs: maximum flow rate Rmax, average flow rate $\bar{R}$, voiding volume V, voiding time $T_v$, flow time $T_f$ (with the voiding time probably containing some time To when $R_i=0$), and time to maximum flow rate $T_{Rmax}$.

The signal processing system comprises a conventional amplifying circuit within the transducer assembly 3, and A/D conversion circuit within a conventional microprocessor, as labelled in FIG. 6, and the conventional printer ("Print Results" in FIG. 6). The voltage signal of the displacement transducer 3 is proportional to the instantaneous flow rate $R_1$. The signal processing system samples the output voltage signal of the displacement transducer 3, labelled "Signal" in FIG. 1, and after amplification and A/D conversion, the signals are calculated by the microprocessor in accordance with the flow chart of FIG. 6, which finally prints out the above-mentioned seven data outputs.

As illustrated in the signal processing flow of FIG. 6, once the elastic cantilever deflects under the urinary flow impact, the displacement transducer generates the voltage signal. The signal processing system begins timing and sampling (bottom of FIG. 6), as is well known, at regular intervals. This produces at each time of sampling a value of instantaneous flow rate ($R_i$), which is stored in memory. The maximum flow rate is obtained ("Find $R_{max}$", FIG. 6) after comparison of the different values of $R_i$. The time to maximum flow rate $T_{Rmax}$ is also stored in the memory. After the conclusion of voiding, the sampling stops and all of the data stored is processed. The sum of all instantaneous flow rate values ("$\Sigma R_i$", FIG. 6) is divided by the number of sampling times n and equals the average flow rate ($\bar{R}=\Sigma R_i/n$), designated by "$\bar{R}$" in FIG. 6). The voiding volume V is determined by integration $V=\int R_i dt$ labeled "Integration to Find V" in FIG. 6. The voiding time $T_v$ ("$T_v$" in FIG. 6) is defined as the time between the begining and ending of sampling. The time when $R_i=O$ is determined as To. $T_v$ minus $T_o$ equals the flow time $T_f$ bottom of FIG. 6.

The uroflowmeter of the invention is thus based on an impulse momentum method of measurement and reflects the dynamic process of voiding, featuring high sensitivity and reliable performance.

Modifications will occur to those skilled in this art and are considered to fall within the spirit and scope of the invention as defined in the appended claims.

What is claimed is:

1. A method of measuring uroflow, that comprises, impacting urinary flow upon an elastic surface to produce flow impulse momentum-generated displacements thereof proportional to the instantaneous flow rate; transducing said displacements into corresponding electrical signals; sampling said signals at periodic intervals and storing the sample signals corresponding to instantaneous values of said flow rate; storing the maximum signal value of such flow rate and its time; determining the value of the average flow rate from the sampled signals; calculating from such signals the urine voiding volume and the time over which the sampling has been taken; determining the flow time from the above; and displaying the above determined and calculated dynamic characteristics of the uroflow.

2. Apparatus for measuring uroflow parameters having, in combination, elastic surface means; means for impacting urinary flow upon said surface to produce flow impulse momentum-generated displacements thereof proportional to the instantaneous flow rate; displacement-measuring transducer means for generating electrical signals corresponding to said displacements; signal processing means responsive to said electrical signals and comprising means for sampling the same and storing the sample signals corresponding to instantaneous values of said flow rate, and means for determining from said signals the maximum and average flow rates, urine voiding volume and flow time; and means for displaying such determined dynamic characteristics of the uroflow.

3. Apparatus as claimed in claim 2 and in which said elastic surface means comprises a cantilever.

4. Apparatus as claimed in claim 3 and in which the urinary flow impacting means comprises an apertured guiding surface causing the flow to pass along tube means to impact upon an end of the cantilever.

* * * * *